United States Patent [19]
Fried et al.

[11] Patent Number: 5,810,590
[45] Date of Patent: Sep. 22, 1998

[54] DENTAL IMPLANTS AND METHODS FOR EXTENDING SERVICE LIFE

[76] Inventors: Paula S. Fried, 207-20 Jordan Dr., Bayside, N.Y. 11360; Leonard Cooper, 999 Grant Ave., Pelham Manor, N.Y. 10803

[21] Appl. No.: 753,887

[22] Filed: Dec. 2, 1996

Related U.S. Application Data

[63] Continuation-in-part of Ser. No. 380,850, Jan. 30, 1995, Pat. No. 5,580,246.

[51] Int. Cl.$^6$ .................................................. A61C 8/00
[52] U.S. Cl. ............................................ 433/172; 433/173
[58] Field of Search .................................. 433/173, 174, 433/175, 172, 176, 75

[56] References Cited

U.S. PATENT DOCUMENTS

| | | | |
|---|---|---|---|
| 2,857,670 | 4/1958 | Kiernan, Jr. | |
| 4,179,810 | 12/1979 | Kirsch | 433/75 |
| 4,416,629 | 11/1983 | Mozsary et al. | 433/174 |
| 4,713,003 | 12/1987 | Symington et al. | 433/173 |
| 4,758,161 | 7/1988 | Niznich | 433/173 |
| 4,762,492 | 8/1988 | Nagai | 433/174 |
| 4,856,994 | 8/1989 | Lazzara et al. | 433/173 |
| 4,886,456 | 12/1989 | Ross | 433/173 |
| 4,955,811 | 9/1990 | Lazzara et al. | 433/173 |
| 5,013,242 | 5/1991 | Prezmecky | 433/174 |
| 5,052,931 | 10/1991 | Kirsch | 433/173 |
| 5,125,840 | 6/1992 | Durr et al. | 433/173 |
| 5,195,892 | 3/1993 | Gersberg | 433/173 |
| 5,205,746 | 4/1993 | Chanavaz | 433/174 |
| 5,368,483 | 11/1994 | Sutter et al. | 433/173 |
| 5,449,291 | 9/1995 | Lueschen et al. | 433/173 |

FOREIGN PATENT DOCUMENTS

| 6178784 | 6/1994 | Japan | 433/174 |
|---|---|---|---|

*Primary Examiner*—Cary E. O'Connor
*Attorney, Agent, or Firm*—Helfgott & Karas, P.C.

[57] ABSTRACT

An implant has a proximal protrusion that is distinctly non-round even in a worn state, e.g. square in cross section, and may include radial slots for use in threading the implant into the jaw bone. No forces need be applied directly to the protrusion's external surfaces when inserting the slotted implant for subsequent osseointegration.

11 Claims, 5 Drawing Sheets

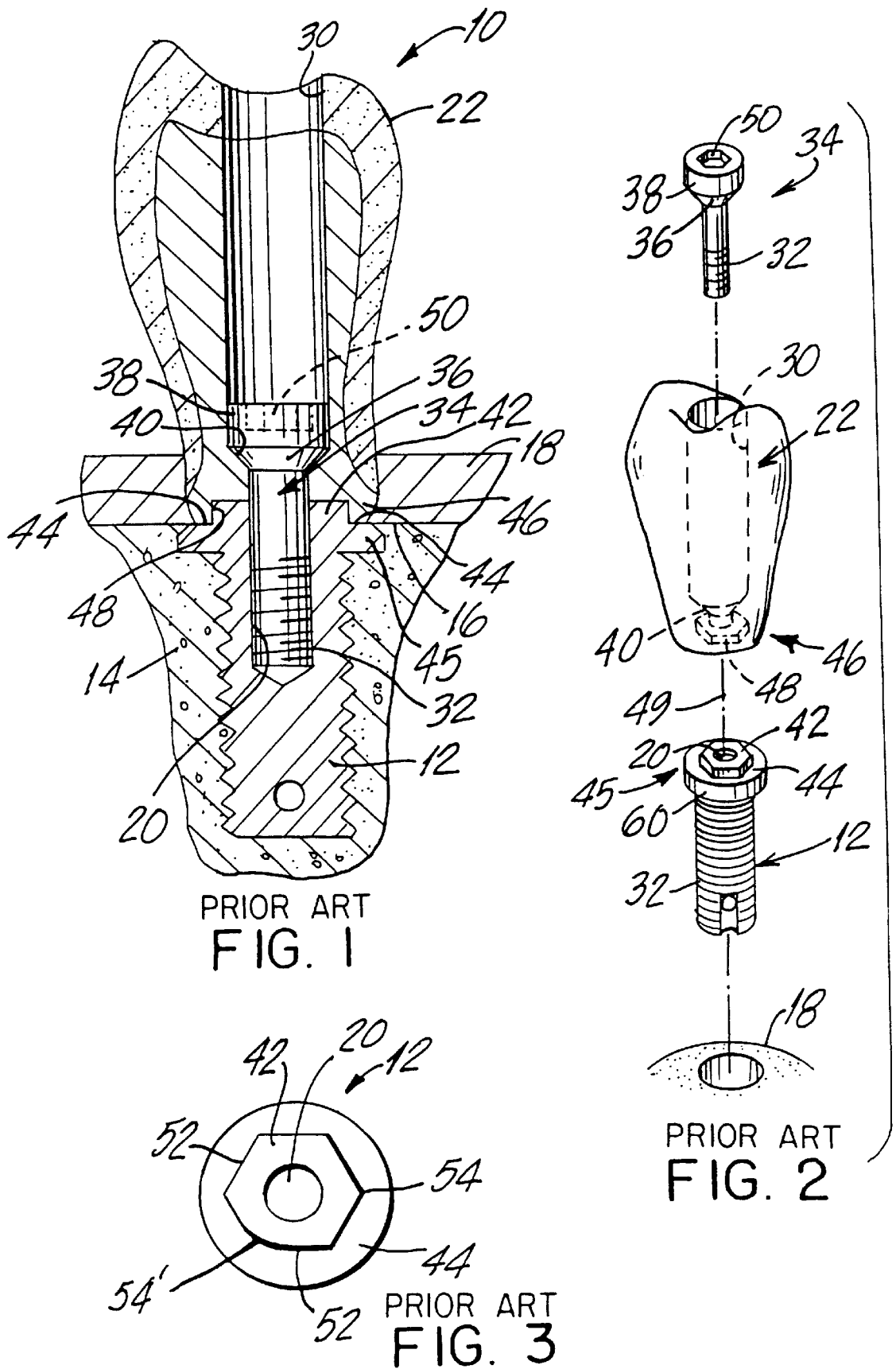

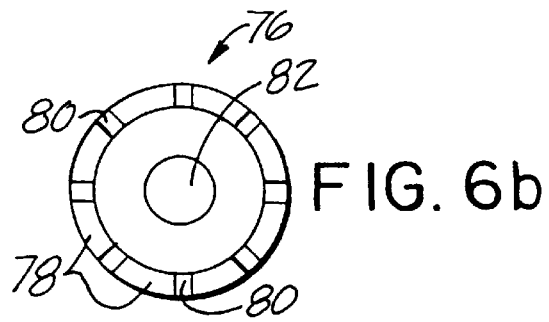
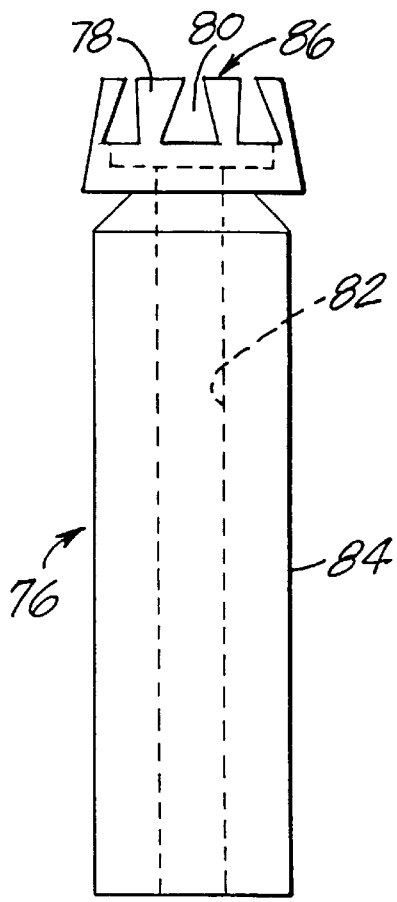
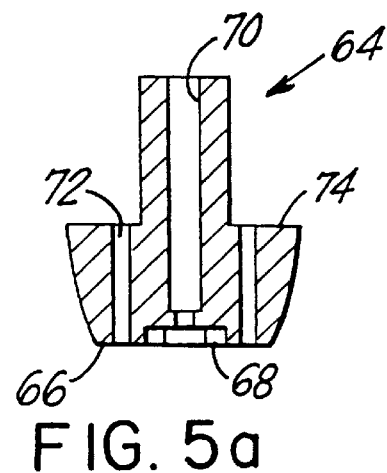
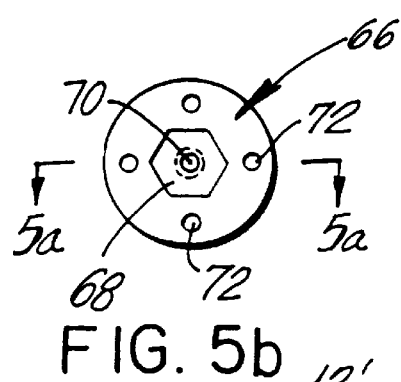
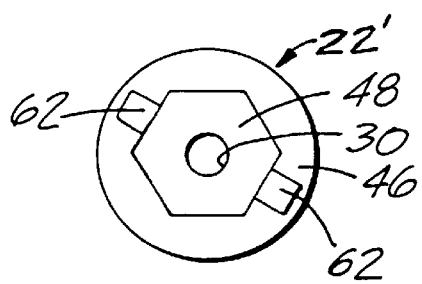
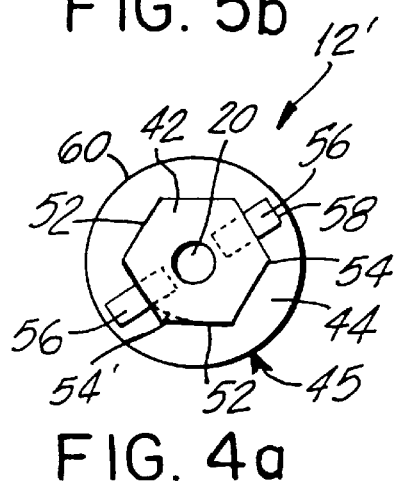

DENTAL IMPLANTS AND METHODS FOR EXTENDING SERVICE LIFE

This is a continuation in part of Ser. No. 08/380,850, filed Jan. 30, 1995, now U.S. Pat. No. 5,580,246.

BACKGROUND OF THE INVENTION

This invention relates generally to a dental prosthesis and more particularly to a dental prosthesis that is attached to an implant in the bone of a person's jaw.

It is now common when it is desired or necessary to replace a missing tooth or teeth, that the gum is opened and an implant is imbedded in the bone structure beneath the gum. The implant is held initially by friction in a socket formed in the bone or the implant may be threaded into the bone. The gum is then closed over the implant and heals. When a proper material is used for the implant, the bone and implant grow together by a process known as osseointegration so that after several months the implant becomes a permanent part of the bone structure in the mouth. Titanium has been an effective implant material.

Many firms manufacture complete systems of dental implants and prosthetic components for subsequent attachment to the implants. In a typical construction, the implant has an axially threaded hole at its top, that is, the proximal end, near the gum surface. After the implant has integrated with the bone, the gum of the implant is opened to expose the tapped hole. Then an abutment is attached to the tapped hole of the implant and extends to a level above the gum or substantially to the gum surface. The protruding free end of the abutment is constructed for attachment of a prosthesis. For preventing rotation of the prosthesis, the protruding end of the abutment requires a non-round shape and a hexagonal protrusion has been widely used. The abutment also includes a central threaded hole concentric with the threaded hole of the implant and extending inward toward the jaw bone.

A false tooth or crown is provided with a hole therethrough, known in the art as a chimney, and a non-round recess in its base corresponds in shape to the protruding non-round cross section of the abutment. Thereby, the crown can be connected to the abutment and relative rotation between them is prevented so long as critical contours of the abutment and the recess in the crown are maintained.

To prevent the crown from lifting axially from the abutment, a final screw, sometimes known in the dental profession as a "gold screw", is passed into the chimney opening and engages the tapped hole in the implant by way of the abutment so as to hold the crown axially to the abutment and to the implant. Thus, the crown cannot rotate about the abutment or implant because it is mated with the special contours on the exposed end of the abutment. The abutment is similarly mated to the proximal or outer end of the implant. The crown cannot pull away from the abutment when the gold screw has been tightened into place.

Finally, the chimney above the gold screw is filled with a composite material that hardens and is shaped as part of the crown to look like a natural tooth.

There are many variations in construction.

In many instances, the crown is attached directly to a non-round protrusion of the implant and is held directly to the implant by a gold screw without use of an intermediate abutment.

The implant is intended to be a permanent fixture in the jaw bone. The abutment and crown may be replaced if necessary due to damage or poor fit by gaining access to the screw head by way of the chimney, and backing off the screw so that the crown and abutment, if used, can be separated from the implant. Thus, repairs may be made of an abutment and crown with relative convenience.

Whereas dental implantations go back to the days of the Pharaohs in Egypt, use of titanium metal implants that integrate with the bone itself, is a recent development over the last 25 to 30 years. Data so far available on the service life of such implants, indicate that most implants can be expected to have a long service life without complications of the implant itself. However, in a significant percentage of implants, a problem arises because titanium is a relatively soft metal. An unacceptable degree of looseness often develops between the implant and the adjacent abutment or crown whereby there is relative rotation between the implant and the attached elements. This rotational latitude occurs when the contours of the protrusion at the proximal end of the implant become worn as a result of lateral forces applied on the protrusion. Such forces are transmitted from the crown as the crown interacts with adjacent teeth, and perhaps bones, during the course of chewing, biting and nervous grinding (bruxism). Tremendous rotational forces are known to act on the crown. Once there is some degree of freedom for rotation of the crown relative to the implant, the non-rounded contours of the implant protrusion tend more and more toward roundness, and permit more and more rotation. In time, the connection between the implant and the abutment and crown connected thereto does not prevent rotation and is unacceptable.

In these types of failure, for example, where the original protrusion on the implant was hexagonal in shape, it has been found that the corners of the hexagonal shape have been rounded to such a degree that it is not possible to attach a new crown or abutment and prevent rotation relative to the implant.

As stated, this type of rounding on the implant protrusion occurs during normal use of the prosthesis in biting and chewing. Also, the contours of the implant protrusion may become distorted, especially unfavorably rounded or stripped, during the process of threading the implant into the jaw bone. This occurs because the implant protrusion is the means by which the driving tool engages the implant. Therefore, when hard bone is encountered, it is possible that an implant may be damaged beyond usefulness by an ill fitting socket type wrench that engages the outer surfaces of the protrusion and is used to drive-in the implant.

This situation, though costly, is not catastrophic when initially inserting an implant in that the damaged implant may be removed and a new one may be inserted. Unfortunately, after the implant has been joined to the jaw bone by osseointegration, and after years of this condition, it is extremely difficult, costly, and the cause of considerable suffering to the patient, to attempt to remove a damaged implant and replace it with another.

What are needed are a method to rehabilitate in the mouth a damaged implant that no longer holds the crown effectively against rotation, and an improved implant that better resists rotation of an attached abutment and/or crown and thus has an extended service life.

SUMMARY OF THE INVENTION

Accordingly, it is an object of the invention to provide a method for rehabilitating the proximal end of an implant so as to prevent relative rotation of abutment or crown elements after the initial attachment means has failed.

Another object of the invention is to provide an improved dental implant that reduces the hazards of damage to the implant attachment protrusion during installation and of damage due to crown rotation during normal usage over the life of the prosthesis.

Yet another object of the invention is to reduce the occasions when an implant that has osseointegrated with the jaw bone needs removal in its entirety.

In a method to rehabilitate or repair an implant having a damaged proximal protrusion, such that there is unacceptable rotation between the implant and an attached abutment and/or crown, a jig is slipped over the remaining implant protrusion after removal of the crown and abutment. Guided by the jig, a burr forms radial slots, or other indentations, in the outer surface of the implant adjacent to the protrusion. The slots or other indentations may extend into the implant protrusion. A new abutment (and/or crown) is prepared by techniques that are a modification of casting techniques well known in the dental arts. The bottom surface of the prosthetic device that engages the implant precisely engages the newly-added radial slots or indentations on the implant such that when the final screw is tightened into place, rotation between the implant and the attachments is prevented.

Modified analog implants, copings, and abutments facilitate the method.

Further, an improved implant in accordance with the invention has a proximal protrusion that is generally square in cross section and further includes radial slots for use in threading the implant into the jaw bone. Thereby, no forces need be applied directly to the protrusion's external surfaces when inserting the implant for subsequent osseointegration. In this way, the surfaces of the protrusion that are used to maintain the abutment and/or crown against rotation relative to the implant are not subject to inadvertent damage during installation of the implant in the jaw bone. Further, the rotation resisting surfaces of the squared protrusion are broad and generally continuous and adjacent surfaces meet at 90° angles, or less. Forces tending to rotate the crown have little effect on the holding power of the proximal protrusion even should the edges of the protrusion be removed or become rounded.

In accordance with the invention, radial slots may be formed into the protrusion itself or extend radially from the base of the protrusion. Slots may be provided in different radial directions.

Further, the slots may be omitted whereby the implant, if threaded into the jaw bone, is driven by a tool applied to the protrusion. Many cross sections are available for the protrusion to provide a non-round shape. These cross sections include regular and nonregular convex and nonconvex polygons, rounded shapes, and fluted surfaces.

The invention accordingly comprises the several steps in the relation of one or more of such steps with respect to each of the others to effect rehabilitation of an implant, and the apparatus embodying features of construction, combinations of elements and arrangement of parts which are adapted to effect extended service life for such implants, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a front elevational view, in section, of an implant of the prior art;

FIG. 2 is an exploded view, in perspective, of the dental implant construction of FIG. 1;

FIG. 3 is a top view of the implant of the prior art;

FIGS. 4a, b are top and bottom views, respectively, of a repaired implant and modified crown, in accordance with the invention;

FIGS. 5a, b are respectively an elevational view, in section, and a bottom view of a notching jig in accordance with the invention;

FIGS. 6a, b are front and top views respectively of an abutment in accordance with the invention;

DESCRIPTION OF PREFERRED EMBODIMENTS

Figure 9:
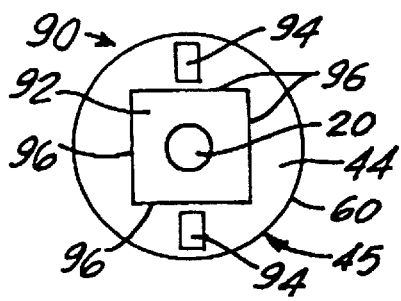
FIG. 9 is a top view of an alternative embodiment of an implant in accordance with the invention.

The present invention is concerned with the problem of rotation of a crown, or an abutment and crown, relative to a dental implant to which the abutment and crown are attached. In many applications, the abutment is omitted and a crown attaches directly to the implant. In every instance, the inherent problem of relative rotation is substantially similar. Accordingly, any description that includes an abutment, or any description that omits use of an abutment, is also applicable to the other construction.

In FIGS. 1–3, a dental prosthesis 10 of the prior art includes an implant 12 embedded in the spongiosa 14 of the jaw bone. After a healing period of several months, the implant 12 has become part of the bony structure by the known process of osseointegration. The implant 12 protrudes through the cortex 16 of the jaw bone, and the gum tissue 18 conceals the proximal end of the implant 12. A tapped hole 20 opens at the proximal end and is accessible between the parted gum tissue 18. The crown 22 usually aligns with the tapped hole 20 in the implant 12.

A hexagonal boss 42 on the implant 12 protrudes above a surface 44 of a flange 45 of the implant 12. The base 46 of the crown 22 includes a hexagonal socket 48, whereby the crown 22 can be removably connected to the implant 12 with the implant boss 42 engaged in the hexagonal socket 48 of the crown 22. Thereby, rotation of the crown 22 about the longitudinal axis 49 of the implant 12 is prevented by the hexagonal cross-section.

Threads 32 of a screw 34 engage the tapped hole 20 until a bevel surface 36 on the screw head 38 engages a shoulder 40 on the crown 22. Tightening the screw 34 into the threaded hole 20 of the implant 12 draws the crown 22 into a rigid axial connection with the implant 12 and consequently with the bony structure 14, 16 of the jaw.

In attaching the crown 22, the screw 34 is tightened by means of an Allen-head type tool that engages the hexagonal socket 50 in the screw head 38. Then the chimney 30 is filled with a filler material, known in the dental arts, and the exposed surface of the filler material is contoured to match the remainder of the crown.

The implant 12 may be screwed into the jaw bone or may be pressed into a prepared socket. When a titanium implant 12 is used, as is the current practice, it is anticipated that an osseointegration process will bind the implant 12 permanently into the jaw after a period lasting three to six months. Then, the crown 22 is prepared to custom fit the integrated implant within the space available between adjacent teeth. Frequently, a gum shaping device or healing cap (not shown) is threaded into the tapped hole 20 and maintained in place while the gum heals after the initial implantation. When screwed into the bone, the implant 12 is driven by attachment of an Allen-head type tool onto the protruding boss 42. To reduce any hazard of damaging the surfaces of the protrusion 42 while tapping (threading) the socket in the bone, an analog implant (not shown) of material stronger than titanium, e.g. stainless steel, may be used. After the socket is tapped, the actual implant 12 is threaded into the prepared opening. Once the final setting is made, hopefully, the implant will never need removal.

FIG. 3 is a top view of the implant 12, clearly illustrating a hexagonal boss or protrusion 42 having six planar surfaces 52 that intersect at apexes 54 with 120° angles between them. However, as the apexes 54 become rounded, as illustrated at 54', due to forces exerted on the crown during chewing, biting, etc., the overall cross section of the boss 42, takes on a circular shape and resistance to further rotational relative motion between the implant 12 and the crown 22, attached thereto by engagement with the boss 42, diminishes to the point where the utility of the prosthesis is compromised. Repair or replacement becomes necessary.

Whereas an attached crown, which is damaged, can be replaced with relative ease, there is no purpose to such a procedure unless steps are taken to prevent future relative rotation between the crown 22 and the implant 12.

By a rehabilitation method in accordance with the invention, the proximal end of the implant 12 is modified in vivo by the addition of slots 56 (FIG. 4a) formed into the surface 44 of the implant 12 adjacent to the boss 42. ("prime" reference numerals, e.g., 12', 22', indicate modified or repaired elements.) The ends 58 of the slots 56 preferably do not extend to the circumference 60 of the flange 45 so as to prevent bacterial action which might otherwise occur in those regions, if the slots 56 left small open pockets at the crown/implant interface.

The lower or bottom surface FIG. 4b of the crown, which may incorporate an abutment, includes a recessed socket 48 wherein the boss or protrusion 42, although deformed, extends. To complement changes in the implant, the undersurface of the new crown 22', in accordance with the invention, also includes protrusions 62 corresponding with the shapes and positions of the slots 56 newly-formed in the implant 12' such that when the prosthesis is assembled, the radially oriented protrusions 62 on the crown 22' engage in the slots 56 on the implant 12' and thereby prevent rotational relative motion between the implant 12' and the crown 22'.

Next will be described methods, in accordance with the invention, for rehabilitating an implant 12 in the mouth to provide the constructions illustrated in FIGS. 4a, b, when the implant can no longer maintain the proper rotational orientation with the crown 22 of the prosthesis. This occurs, for example, because the apexes 54 on the hexagonal boss 42 have become rounded due to the inherent softness of the titanium metal and the tremendous forces exerted on the crown during chewing, biting, etc.

First, the proximal end of the implant 12 is exposed by removal of the crown 22 and an abutment, if one was used intermediate the implant and the crown. As a result, the protrusion or boss 42 and the surface 44 on the implant are exposed to view (FIG. 3).

These external elements are removed after exposing and backing out the screw 34 via the chimney 30. Then a notching jig 64 (FIGS. 5a, b) is placed onto the implant 12. The notching jig 64 includes a bottom interface surface 66 that rests on the exposed flange surface 44 of the implant 12. A hexagonal socket 68 extends into the bottom surface 66 of the jig 64, having dimensions such that the protrusion or boss 42 on the implant 12 enters the socket 68 when the surfaces 66, 44 of the jig and implant are in contact. It should be understood that the socket 68 may be round in section so long as the boss 42 enters and allows seating of the jig 64 with a relatively snug fit to provide alignment.

The notching jig 64 has a long stem with a longitudinal opening 70 through which a threaded screw (not shown) is inserted so as to engage the central opening 20 in the implant 12. Thus, the jig 64 is axially fixed into position on the implant 12 even though the boss 42 is worn. Guide holes 72 extend from a rear shoulder 74 on the jig 64 to the interface surface 66. Four guide holes 72 are illustrated; in practice, two guide holes are sufficient when two slots 56 are to be formed in the implant surface 44.

With the notching jig 64 in place on the implant 12, the dental practitioner runs a rotating burr through the guide holes 72, in turn, and forms indentations 56 into the upper surface 44 on the flange 45 of the implant 12. A stop on the burr or shoulders (not shown) within the guide holes 72 limit the depth of the indentation 56 formed in the surface 44 of the modified implant 12'. Thus, a configuration as shown in FIG. 4a, albeit with less precisely rectangularly shaped slots 56, is produced. The burr shaft diameter, used to make the indentations or slots 56 on the surface 44 of the implant, may be less than the diameter of the guide holes 72, giving the practitioner latitude of motion so as to shape the slots 56 in the implant 12'.

Alternatively, the guide holes 72 may be radially oriented ovals (not shown), extending inwardly toward the opening 20 so that the burr may provide extended slots in the implant 12 that cut into the protrusion 42. These elongated slots, the extensions indicated in FIG. 4a with broken lines on the boss 42, may extend nearly into the tapped hole 20. The longer slot provides a stronger engagement with a driving tool and with the modified crown, which is provided with longer protrusions 62.

In another embodiment of the method for repair, a notching jig may provide slots only into the boss 42 and not in the flange surface 44.

Repair of an implant already imbedded in the jaw bone and osseointegrated has been described above, describing the indents formed into the implant as "slots". It should be understood that indentations having contours other than the radial slots illustrated in FIG. 4A may be provided in the exposed surface of the implant so long as correspondingly configured protrusions are provided on the mating element, for example, the crown or abutment.

It is now necessary that the abutment and crown which ultimately attach to the modified implant 12' be made to precisely mate with the slots 56 (or other indentations) formed on the surface 44 of the implant. For the sake of the following description of repair procedures, it is assumed that no separate abutment element is used intermediate the implant and the crown in the completed prosthesis. Further, generally rectangular slots are described; the procedures also apply to indentations of other shapes.

How to make a crown for attachment to an osseointegrated implant in the jaw is well known in the art of dental implants. The same basic procedures are followed in making a crown for the now-modified dental implant 12', which is still embedded in the jaw bone, however with slight changes in the elements that are used to accommodate the slots now formed in the flange surface 44 of the implant 12'. The finished crown must have protrusions on its lower inner surface that interface with the implant to complete the prosthesis.

Figure 8:
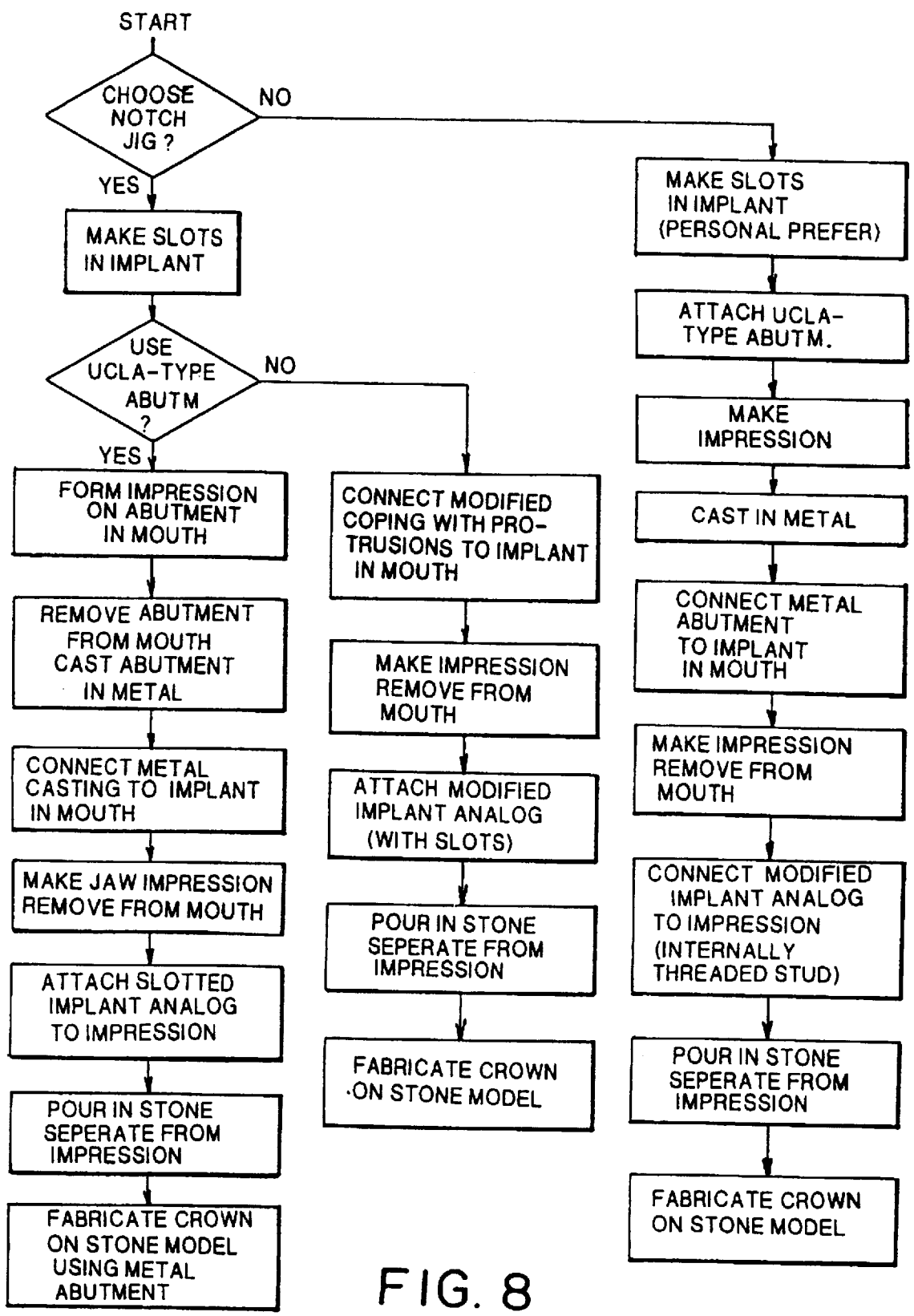
FIG. 8 is a flow diagram of methods in accordance with the invention to produce a repaired dental prosthesis.

Therefore, conventional fabrication techniques using a direct pick up impression or an indirect impression would readily be implemented by those skilled in the implantation art without further explanation. However, a brief description (and flow diagram FIG. 8) is given of several techniques to indicate how the modifications made at the proximal end of the implant affect the procedures.

In a direct pickup technique, after notches or slots 56 are prepared on the implant 12' with the notching jig 64, as described above, a direct impression of the modified top of the implant 12' is made by customizing a resin UCLA-type abutment, using a well-known auto-polymerizing resin. FIGS. 6a, b illustrate a customized resin UCLA-type abutment 76 made of plastic and having teeth 78 with novel dove-tail spaces 80 between them such that impression material after hardening, will not separate from the abutment although the impression material does bond to the resin abutment.

The customized abutment 76 is attached to the implant 12' by a guide pin (not shown) that passes through the longitudinal opening 82 in the stem 84 of the abutment 76 and engages the tapped opening 20 in the implant 12'. Then the impression material is applied to fill the spaces between the abutment 76 and the implant surface 44. After the impression material has hardened, the guide pin is unscrewed from the implant 12' and the abutment 76 is removed. Covering the end 86 of the abutment 76 that opposed the implant 12', protrusions 62 are present exactly corresponding to the slots 56 newly formed on the implant 12'.

Then, the customized abutment impression (not shown) is cast into a strong, rigid material e.g. metal. The resultant metal abutment is placed over the implant 12' in the jaw, and is secured in place with a guide pin that engages the central opening 20 of the implant 12' by passing through a central opening in the metal abutment that corresponds to the opening 82 that was in the customized UCLA-type abutment 76. The protrusions 62 are seated in the implant slots 56.

Then a pick-up impression is made in the mouth in the conventional manner, that is, a window is cut in the top of an impression tray; the tray is filled with impression material and some of this material is positioned around the abutment. Then the filled impression tray is placed over the implant 12' and metal abutment with the guide pin protruding through the impression material and from the upper surface of the tray. After the impression material has hardened in the tray, the guide pin is unscrewed and the impression tray with the metal abutment now embedded in the impression, is removed from the mouth. The protrusions 62 on the face of the metal abutment are visible in the impression.

A modified implant analog (stainless steel) having slots that correspond with the slots 56 which were formed using the jig 64, is positioned on the abutment with the slots on the implant analog receiving therein the protrusions 62 on the metal abutment, which was embedded in the impression. The implant analog is fixed to the abutment with a guide pin, and the assembly is poured in stone, that is, a rigid modeling material. After hardening, the guide pin is removed, and the impression containing the abutment is separated from the stone.

The stone model now positively replicates the portion of the jaw including the implant 12'. The model includes the analog implant with slots having the exact same dimensions and orientation as those slots 56 in the actual implant 12' in the jaw bone of the patient.

The metal abutment is now removed from the earlier impression material. The metal abutment was made with protrusions 62 that exactly mate with the analog implant. From this state, a crown is fabricated by well known procedures. The crown incorporates the metal abutment, thus assuring a perfect fit for the crown in the mouth.

Rotation of the crown relative to the modified implant 12' is prevented by engagement of the protrusions 62 from the abutment with the slots 56 in the exposed surface 44 of the implant 12'.

In a conventional indirect impression technique, slots 56 (FIG. 4a) are prepared in the implant 12 in the jaw using the notching jig 64. An impression coping is attached to the implant 12' using a guide pin (not shown); the impression coping is conventional except that it has protrusions on its lower surface that correspond with the slots 56 made in the actual implant 12 when the notching jig 64 was used. The drawing of the bottom of a crown (FIG. 4b) in accordance with the invention also illustrates the modifications (protrusions) to a conventional impression coping's bottom interface surface. Thus, a proper engagement between the prefabricated coping and the implant 12' is assured.

Then an impression tray with a window cut out of the top is placed over the implant and surrounding portion of the jaw so that the guide pin protrudes. The tray is filled with impression material in a conventional manner. After the impression material has set, the guide pin is unscrewed and the impression is removed from the mouth. An implant analog (e.g. stainless steel) is then abutted with the coping in the impression, with slots being provided on the implant analog to mate with the protrusions, which are extending from the surface of the impression coping. After the implant analog abuts the coping in the impression, the analog and coping are secured together with a guide pin, and a model is poured in stone. The stone model replicates, at least partially, the jaw of the person, however, with the proximal end of the implant analog exposed to view, including its slots in the proper orientation. Then a crown is fabricated by conventional procedures. New materials, namely nylon, gold and aluminum oxide ($Al_2O_3$) may be used in fabricating the crown on the stone model in this technique.

In the above methods, it has been assumed that the drill jig 64 is used in modifying the implant 12 in the jaw. When this is done, the hardware, namely the copings and analog implants, are pre-manufactured, off-the-shelf items with protrusions and slots that will fit or match the slots that were made in the actual implant in the jaw bone.

However, many practitioners will prefer not to use such a jig 64 and will instead produce a variety of indentations of their own preference on the surface 44 of the implant 12 in the mouth. In such a situation, pre-manufactured implant analogs and pre-manufactured copings with the proper patterns of slots and protrusions, as required, will not be available off-the-shelf.

Figure 7:
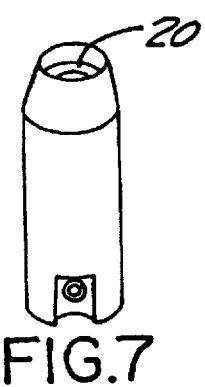
FIG. 7 is a perspective view of a modified implant analog.

Therefore, to practice the above procedures, it is necessary to first make a direct pick up from the implant 12' in the mouth, using a customized UCLA-type abutment 76 (FIGS. 6a, b) as described above. This impression is then cast in metal and the first procedure as described above is followed with the exception that a modified implant analog must be used in the stone-pouring step. This modified implant analog (FIG. 7) does not have a flange 45 or boss 42 but is primarily a shank that is internally threaded. Before casting in stone, the modified implant analog is held to the metal abutment in the earlier-formed impression by a guide pin that threadably engages the analog. Then the stone is poured. (Epoxy may be used alternatively in pouring this model) The stone model of the jaw will have the central threaded opening of the analog implant exposed to view. However, the surface with the corresponding slots of the true implant is reproduced in the stone material. From that state, fabrication of a crown is conventional, as before.

Next, an embodiment of an implant in accordance with the invention is discussed, which will reduce the hazards of stripped and damaged boss surfaces that would in time prevent proper mating with an abutment and/or crown. The same reference numerals are used in the description of the improved implants where elements correspond to those of FIGS. 1–6.

In an implant 90 of FIG. 9, a boss 92 having a cross section that is a rectangle, in this instance a square, as compared to the hexagonal boss of the prior art, is elevated above the surface 44 of a flange 45 on the implant 90. As in the earlier embodiments, a tapped hole 20 is at the center of the surface 44, and a screw 34 ultimately seats in the hole 20 to hold a crown, with an abutment in place. Short slots 94 are recessed into the surface 44 at opposed sides 96 of the square boss 92. The slots 94 do not reach to the outer circumference 60 of the flange 45 in order to avoid potential bacterial activity at those sites.

Each of the sides 96 of the boss 92 have a greater continuous length as viewed in FIG. 9 than any single side of the hexagonal boss 42 of the prior art (FIG. 3) for a corresponding circumference 60. Thus, when, for example, a crown with a square recess on its bottom surface is fitted to the implant 90 with a snug fit to the boss 92, and is tightened in place with a screw 34, there is little likelihood that the attached crown will ever rotate relative to the implant. The parallel opposed sides 96 and included 90° angle of the square boss 92 prevent rotation even if the corners of the square-shape should for some reason become rounded.

The boss 92 is bevelled (similar to FIG. 10b) at its upper edges 93. Also, the boss 92 may rise vertically from the general plane of the surface 44 or there may be a slight taper in the direction away from the flange 45. Such a construction makes for easier entry of the boss 92 into a recess, which may also have tapered sides, for example, in a crown.

Additionally, the slots 94 are provided for the purpose of screwing the implant into the bone. The bone is frequently pretapped using a dummy (analog) implant that is made of tougher metal or plastic than the titanium implant itself. The tool which is used for threading the implant 90 into the bone of a patient (not shown) is constructed such that it rotates the implant 90 by tool engagement with the slots 94 and not because of any driving engagement with the sides 96 of the boss 92. Thus, the surfaces of the boss 92 do not become damaged by the insertion tool upon the initial installation of the implant into the jaw bone, and the contours of the boss 92 are preserved for accurate and effective mating with the abutment and/or crown.

To further assure the fixed relative position between the implant and that which is externally attached to it, the abutment or crown that interfaces with the implant 90 may be made with protrusions that engage in the slots 94 at the interface.

It should also be understood that because of the increased strength of the square boss 92, the boss may be used when threading the implant into the jaw bone, and the slots 94 may be omitted. In such a use of the boss 92, the likelihood of serious damage to its surfaces, so as to render its attachment to an abutment and/or crown rotationally unacceptable, is much less than with the hexagonal boss 42 of the prior art.

Figure 10A:
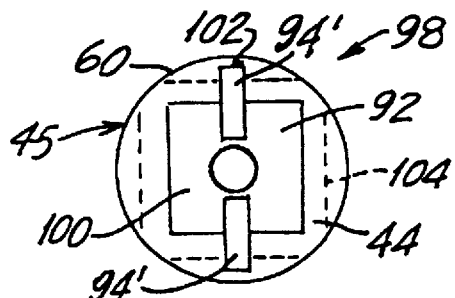
FIG 10a and 10b are a top and side elevation, in section, of another implant of the invention.
Figure 10B:
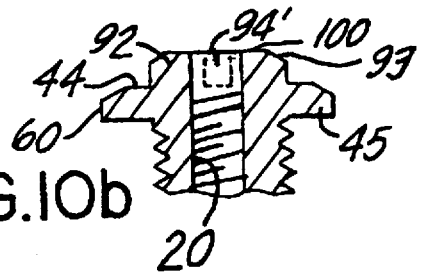

The implant 98 of FIGS. 10a, b, is similar to the implant 90 of FIG. 9 except that the slots 94' extend through the boss 92 near to the central opening 20, such that a blade type tool may be used in the slots 94' when screwing the implant 98 into the jaw bone.

The slot 94' may penetrate in depth into the upper surface 100 of the boss 92, as illustrated with the solid lines in FIG. 10a. On the other hand, the slot depth may be extended (not shown) substantially, even into the flange 45, that is, below the surface 44 of the flange 45. In any event, the slot ends 102 do not extend through to the outer periphery 60 of the flange 45 to reduce hazards of bacterial activity. It is also desirable for similar reasons that the slots do not open into the tapped hole 20.

For the purpose of increased strength of the boss 92, if needed, it is possible in manufacture to enlarge the size of the generally square shape and possible lose the perpendicular intersections as indicated by the broken lines 104 in FIG. 10a. (In all constructions, there is a trade-off between the implant strength and the strength of the attached device.)

Figure 11:
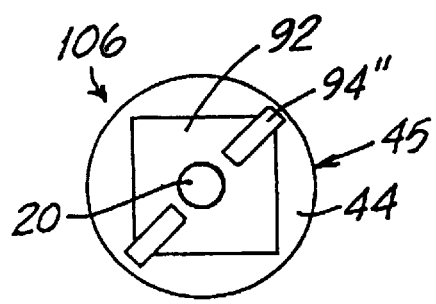
FIGS. 11–14 are additional embodiments, in top view, of implants of the invention.

In FIG. 11 another embodiment of an implant 106 in accordance with the invention is shown having a generally square elevated boss 92 with slots 94" running diagonally across the square and extending proximate to the central opening 20. This provides a longer slot length in the boss itself, but is otherwise similar to the implant 98. As with the implant 98, the slot 94" can penetrate the boss 92 to various depths and may extend to and penetrate into the flange 45.

Figure 12:
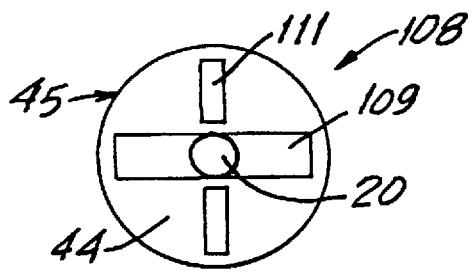

Another alternative embodiment (FIG. 12) provides an implant 108 with an elongated rectangular boss 109 with perpendicularly oriented slots 111 that extend proximate to the central opening 20. The slots are preferably used exclusively for threading the implant into the jaw bone and the boss 109 is preferably used exclusively for holding the abutment and/or crown against rotation. However, with a proper tool (not shown) applied to the boss, the implant may be threaded into the jaw bone.

Figure 13:
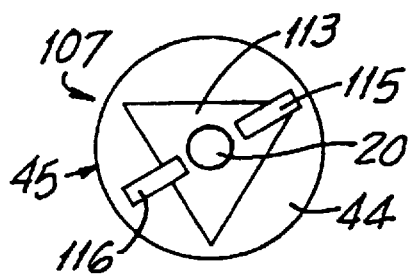

In FIG. 13, an implant 107 includes a generally triangular boss 113 that is penetrated by slots 115, 116 of extended length and selectable (in manufacture) depth that pass through an apex of the triangle.

Figure 14:
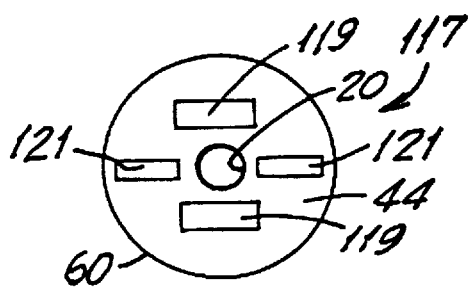

In FIG. 14, an implant 117 includes a pair of rectangularly shaped bosses 119 on opposite sides of the tapped hole 20. A pair of radial slots 121 extend from opposite sides of the tapped hole 20. In using such an implant 117, the crown 22' may have a recess (not shown) on its bottom of rectangular shape that receives both bosses 119 in a single cavity. The bottom surface of the crown may also have protrusions to enter the slots 121. Alternatively, the bottom surface of the crown may have two smaller rectangular recesses with each of the bosses 119 being received in a respective recess. Protrusions to engage the slots 121 may also be a part of the bottom surface of the crown.

In installing such an implant 117 into the jaw bone, it is preferable that a tool that engages the slots 121 is used without engagement with the protrusions 119 for driving purposes. However, it should be understood that the bosses 119 can be used in driving the implant 117 into the jaw bone and a driving tool can be made for that method. Further, both the slots and the bosses may be used when driving the implant into the jaw bone when a properly mating tool is provided. The implant in FIG. 14 may be considered as a variation on the implant of FIG. 12 in that the two bosses 119 are at opposite ends of an elongated rectangular shape.

In each embodiment, it is intended that the implant be threaded into the jaw bone using only the slots in the proximal implant end. Nevertheless, it is recognized that the boss outlines, whether square, elongated rectangular, triangular, etc., because of their cross sectional bulk and long sides with reduced intersection angles present considerably more resistance to deformation than the prior art hexagonal cross section of the boss 42 (FIGS. 1–3).

Further, it should be understood that the hexagonal boss, or any shape of the prior art, may be retained (FIG. 4) in an improved implant with extended slots formed through the boss itself, extending toward the tapped opening 20. In such a modified conventional implant or new manufacture, the implant may be tapped into the bone at its final installation using the slots, without reliance on the contours of the hexagonal boss itself. In this way, the boss is protected from damage during installation of the implant.

Figure 15:
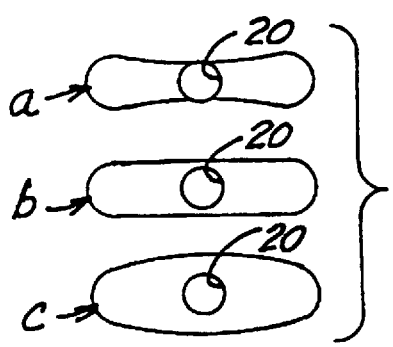
FIG. 15 presents top views of alternative bosses in accordance with the invention.

Whereas the figures have illustrated bosses having different polygonal cross sections that are defined by straight lines and crisp intersections of those lines, it should be understood that rounded and bevelled edges, are intended to fall within the scope of the invention. Additionally, any generally axially oriented side surface of a boss may include a bulge or concavity so long as the basic polygonal shape is retained. For examples, FIG. 15 illustrates an elongated rectangular boss that has rounded ends so as to be an oval b. The long sides are concave in a and bulging in c. These are variations of the boss, for example the rectangular boss in FIG. 12, and for the purposes of this disclosure, are considered to be elongated rectangular (polygonal), possibly including straight and rounded segments, and fall within the scope of the invention. As stated, a trade off must be made between the strength of the boss and the strength of the crown to be attached thereto. The concave configuration a may be used where greater strength is required in the crown, and the bulging configuration c in FIG. 15 may be used where the boss requires increased strength.

Figure 16:
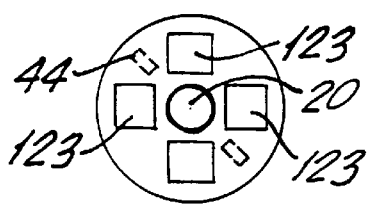
FIGS. 16–18 are further alternative embodiments, in top view, of implants in accordance with the invention.
Figure 17:
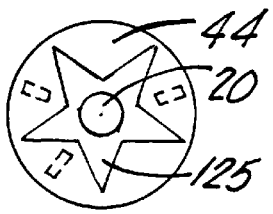
Figure 18:
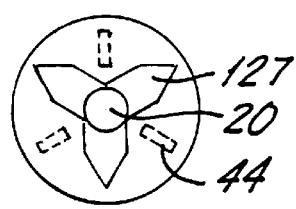

FIGS. 16, 17 and 18 illustrate further alternative embodiments in accordance with the invention of bosses provided with other polygonal cross-sections. In FIG. 16 four rectangular protrusions or bosses 123 project from the surface 44 to be received in corresponding mating recesses on the crown or abutment. Slots (broken lines) or indentations in the surface 44 may optionally be positioned between the bosses 123. Two or four slots may be used. The plurality of protrusions or bosses 123, considered together, provide a non-round shape.

FIG. 17 illustrates a star-shaped polygonal boss 125 extending above the surface 44. Slots or indentations in the surface 44 may optionally be provided as illustrated with the broken lines.

FIG. 18 illustrates a multi-sided polygonal boss 127 rising from the surface 44 in the form of a trefoil. Again, optional slots are illustrated in broken lines as a trio symmetrically positioned in the surface 44 for use in driving the implant into the bone upon initial implantation.

Additionally, in the discussions above, the implants are described as having a central tapped opening 20. However, implants are known in the art wherein the central opening is not tapped and may have a non-round cross-section. In such cases, the crown assembly has a post that extends into the central opening of the implant and an adhesive is used to prevent axial motion of the crown relative to the implant after the adhesive has set. A non-round boss as described above in accordance with the invention prevents the rotation of the crown relative to the implant.

Further, the use of screws that pass through the jaw bone and the implant, and in some instances through the post on the crown that is received in a central opening of an implant, is known in the art, for example, U.S. Pat. No. 5,542,847. All such means for maintaining the axial relationship between the crown and the implant when combined with the bosses, slots etc. in accordance with the invention, are intended to fall within the scope of the invention.

Generically speaking, the cross-sectional shape of the boss in accordance with the invention is made non-round such that should the linear edges extending from the surface 44 become rounded there would remain a distinct non-round cross section for the boss. The hexagonal shape of the prior art and any regular polygon cross section having five, six or more regular sides is vulnerable to circular rounding as vertical edges become worn.

On the other hand, convex polygons as shown, for example, in FIGS. 9–16, present non-round cross sections for the bosses even when the vertical edges become worn and rounded. Additionally, many nonconvex polygons would make excellent boss cross sections and retain their non-round shape and utility even when the linear axial edges are rounded. Further, in production such bosses can be made with beveled or rounded edges, and still be effective for implants.

Further, a generally circular boss cross section can be given holding power against turning by an abutment or crown by use of axially oriented flutes that are formed internally, or externally as teeth. Basic shapes, such as a triangular or square cross section boss may also have supplemental internal or external flutes. Regular hexagonally shaped bosses, by addition of internal and/or external flutes or other formations, maintain a non-round cross section when the axial edges are rounded.

FIGS. 19a–19m show further alternative embodiments of implants in accordance with the invention. In each instance the protrusion from the surface 44 provides a distinctly non-round cross section while providing good anti-rotational anchorage for an abutment or crown combination regardless of wear that may occur along the vertical edges, as seen in the top views in FIGS. 19a–m. Each implant has a central opening 200 that may be threaded or non-threaded depending upon the construction of the prosthesis.

Figure 19A:
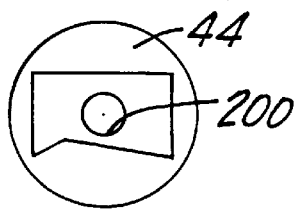
FIGS. 19a–19m are further alternative embodiments, in top view, of implants in accordance with the invention.
Figure 19B:
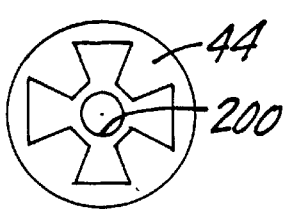
Figure 19C:
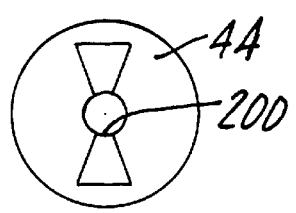
Figure 19D:
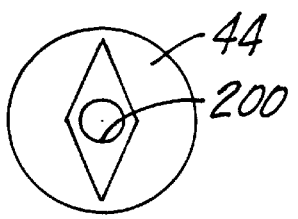
Figure 19E:
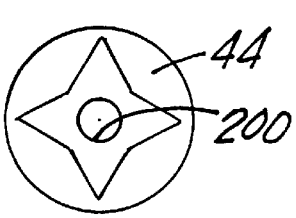
Figure 19F:
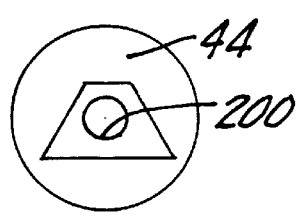

Bosses with cross sections that are convex polygons are illustrated in FIGS. 19d, f, g, and i. FIG. 19c can be considered as a combination of two convex polygons (triangles) in opposed positions relative to the opening 200, or the cross section of FIG. 19c can be considered in its entirety as a nonconvex polygon.

Figure 19G:
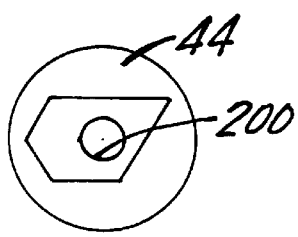
Figure 19H:
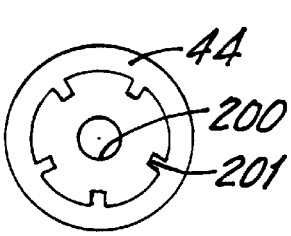
Figure 19I:
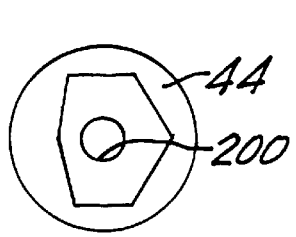
Figure 19J:
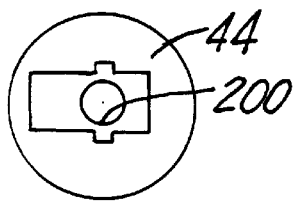
Figure 19K:
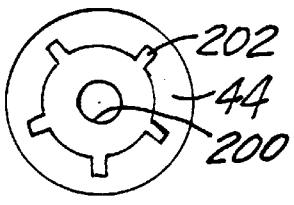

Nonconvex polygons are illustrated in FIGS. 19a, b, e, j, and m. FIGS. 19h and 19k illustrate generally circular bosses that have been given anti-rotational holding power for an abutment or crown by means of internal flutes 201 and external flutes 202, respectively. FIGS. 19g and 19i show cross sections that are distortions of regular hexagons such that a non-round shape is provided even if the vertical edges at the vertices of intersecting sides were rounded.

Each of the polygons can be altered such that sides become concave or convex curves and corners can be rounded so long as the resultant shape retains the desired non-round characteristic that resist turning and wear by an attached prosthesis element. For example, the boss of FIG. 19g takes on a teardrop shape when the vertical edges are rounded. For enhanced holding power, internal or external flutes may be added to any side surface of the cross sections.

Figure 19L:
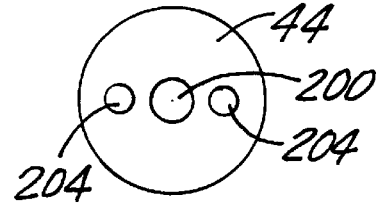
Figure 19M:
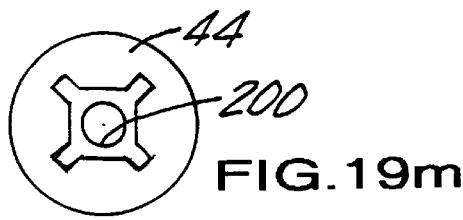

FIG. 19l illustrates the use of circular bosses or protrusions 204 in a symmetrical distribution around the central opening 200. Three, four, or more such protrusions 204 may also be used. The illustrated combination of protrusions in FIG. 19l can be considered a variant of the cross section shown in 15b. A driving tool usable on the configuration of 15b might also serve with the embodiment of FIG. 19l. The combination of protrusions 204, considered together, provides the desired non-round cross section.

In each of the embodiments 19a–m, indentations (not shown) may be provided into the surface 44 for use in threading an implant into the jaw bone, as discussed above.

For the purposes of the descriptions above and the claims that follow, the definitions of different polygons and their features are based upon the school text: Addison-Wesley Geometry, by Stanley R. Clemens, Phares G. O'Daffer, Thomas J. Cooney, John A. Dossey; Addison-Wesley Publishing Co., Inc. Menlo Park, Calif. (1994). In particular, pages 135–140 and later pages, are a source of definitions.

A convex polygon is defined as one in which all diagonals are interior. A nonconvex polygon is one where not all diagonals are interior. A regular polygon is equiangular and equilateral. A trapezoid is a quadrilateral polygon with one pair of parallel sides. A polygon has n sides with the sides meeting at vertices.

Thus, methods for repairing damaged implants in the mouth, and improved implants have been presented. All of those devices that engage the repaired implant, are provided with recesses and protrusions, as required. However, a crown, for example, having a recess with a square cross section so as to match an implant of FIG. 10a, need not have protrusions that match the slots 94', as these slots are basically intended for installing the implant in the jaw bone. Nevertheless, as a redundancy measure and for additional anti-rotation resistance, protrusions on the crown's lower surface that correspond with the slots may also be included in conjunction with the squared recess.

It is contemplated that in practicing the methods, a kit of parts will be purchased from a dental supplier. The kit for those practitioners using preferred methods includes a notching jig 64 and an appropriate burr (not shown) to fit the guide holes 72. Also in the kit may be an implant analog having preformed slots 56 on its proximal end, and an impression coping having protrusions 62 on its lower end. A modified UCLA-type abutment with dove-tail teeth may also be in such a kit, although it could be purchased separately. A different kit for a practitioner who prefers not to use the notching jig may instead include a UCLA-type abutment and a modified implant analog that has no flange 45.

It should also be understood that a reversal of features is intended to fall within the inventions scope. Thus any boss cross-section which has been described as protruding from the flange surface 44 may also be formed (and viewed in the Figures) as a recess in the surface 44. In such a construction the mating crown or abutment is fabricated with a correspondingly shaped protrusion (or protrusions) that seat(s) in the recess (or recesses).

It will thus be seen that the objects set forth above, among those made apparent from the preceding description, made in carrying out the above methods and in the articles set forth without departing from the spirit and scope of the invention, it is intended that all matter contained in the above description and shown in the accompanying drawings shall be interpreted as illustrative and not in a limiting sense.

What is claimed is:

1. A dental implant for insertion in the jaw bone of a patient, comprising:

an elongated body having a longitudinal axis and a proximal surface generally transverse to said longitudinal axis, a boss extending from said proximal surface, said boss having a transverse face, generally axial extended side surfaces, and a non-round cross section as viewed along said axis, at least one indentation penetrating at least one of said proximal surface and said transverse face of said implant.

2. A dental implant as in claim 1, wherein said non-round cross section is polygonal.

3. An implant as in claim 1 wherein said non-round cross section is defined by said side surfaces and selected from the group consisting of a convex polygon, nonconvex polygon, a closed periphery of curved surfaces, and a closed periphery being a combination of curved segments and linear segments.

4. A dental implant as in claim 1, wherein said non-round cross section is selected from the group consisting of generally square, hexagonal, pentagonal, elongated rectangular, oval, triangular, star-shaped, trefoil shaped, trapezoid-shaped, rounded with fluting, polygonal with fluting, non-convex polygonal, and nonregular polygonal.

5. An implant as in claim 1, wherein said side surfaces have flutes, said flutes being selected from the group consisting of internal flutes and external flutes.

6. A dental implant as in claim 1, wherein said boss includes a plurality of protrusions from said proximal surface, said protrusions from said proximal surface considered together providing said non-round cross section.

7. A dental implant for insertion in the jaw bone of a patient, comprising:

an elongated body having a longitudinal axis and a proximal surface generally transverse to said longitudinal axis, a boss extending from said proximal surface, said boss having a transverse face, axial extended side surfaces, and a non-round cross section as viewed along said axis, said non-round cross section being defined by said side surfaces and selected from the group consisting of a convex polygon, nonconvex polygon, a closed periphery of curved surfaces, and a close periphery that is a combination of curved segments and linear segments, wherein said boss includes a plurality of protrusions from said proximal surface, said protrusions from said proximal surface considered together providing said non-round cross section.

8. A dental implant as in claim 7 wherein said non-round cross section is selected from the group consisting of generally square, hexagonal, pentagonal, elongated rectangular, oval, triangular, star-shaped, trefoil shaped, trapezoid-shaped, rounded with fluting, polygonal with fluting, non-convex polygonal, and nonregular polygonal.

9. A dental implant for insertion in the jaw bone of a patient, comprising:

an elongated body having a longitudinal axis and a proximal surface generally transverse to said longitudinal axis, a boss extending from said proximal surface, said boss having a transverse face, axially extending side surfaces, and a non-round cross section as viewed along said axis, said non-round cross section being defined by said side surfaces and selected from the group consisting of generally trefoil, quatrefoil, trapezoid, convex polygon with noncongruent sides, nonconvex irregular polygon, nonregular polygon, tear-shaped convex, and nonrectangular parallelogram cross sections.

10. An implant as in claim 9, wherein said side surfaces have flutes, said flutes being selected from the group consisting of internal flutes and external flutes.

11. An implant as in claim 9, wherein said boss cross-section is asymmetric relative to said longitudinal axis.

* * * * *

UNITED STATES PATENT AND TRADEMARK OFFICE
CERTIFICATE OF CORRECTION

PATENT NO. : 5,810,590
DATED : SEPTEMBER 22, 1998
INVENTOR(S) : Paula S. Fried, et al.

It is certified that error appears in the above-indentified patent and that said Letters Patent is hereby corrected as shown below:

On the title page, item (76), please delete"207-20 Jordan Dr., Bayside, N.Y. 11360" and insert--250 East 63rd Street, Apt. 19C, New York, New York 10021--.

Signed and Sealed this

Second Day of February, 1999

Attest:

Attesting Officer

*Acting Commissioner of Patents and Trademarks*